(«12») United States Patent
Mosaddegh

(10) Patent No.: US 11,103,417 B2
(45) Date of Patent: Aug. 31, 2021

(54) MEIBOMIAN GLAND ROLLER

(71) Applicant: Lillie A. Mosaddegh, San Francisco, CA (US)

(72) Inventor: Lillie A. Mosaddegh, San Francisco, CA (US)

( * ) Notice: Subject to any disclaimer, the term of this patent is extended or adjusted under 35 U.S.C. 154(b) by 199 days.

(21) Appl. No.: 15/143,348

(22) Filed: Apr. 29, 2016

(65) Prior Publication Data
US 2016/0317379 A1    Nov. 3, 2016

Related U.S. Application Data

(60) Provisional application No. 62/155,174, filed on Apr. 30, 2015.

(51) Int. Cl.
*A61H 15/02* (2006.01)
*A61H 15/00* (2006.01)
*A61F 7/00* (2006.01)

(52) U.S. Cl.
CPC .............. *A61H 15/02* (2013.01); *A61F 7/007* (2013.01); *A61H 15/0092* (2013.01);
(Continued)

(58) Field of Classification Search
CPC .. A61H 7/00; A61H 7/001–005; A61H 7/007; A61H 15/00–02; A61H 2201/02–0207; A61H 2201/0221–0235; A61H 2201/1671; A61H 2201/1688; A61H 2201/5082; A61H 2201/5097; A61H 2205/024; A61H 2230/50–505; A61F 2007/004; A61F 2007/0078;
(Continued)

(56) References Cited

U.S. PATENT DOCUMENTS 1,710,051 A * 4/1929 Giacopazzi ........ A61H 15/0085
601/127
3,699,952 A * 10/1972 Waters .................. A46B 13/02
601/18
(Continued)

OTHER PUBLICATIONS

Blackie et al., "Treatment for meibomian gland dysfunction and dry eye symptoms with a single-dose vectored thermal pulsation: a review," Current Opinions in Ophthalmology 26(4): 306-313, Jul. 2015.
(Continued)

*Primary Examiner* — Rachel T Sippel
(74) *Attorney, Agent, or Firm* — Haynes and Boone, LLP

(57) ABSTRACT

A Meibomian Gland Roller system allows for self-administered the treatment for a leading cause of dry eyes, namely, tear film oil deficiency. The system combines an effective and safe technique to combine mechanical rolling pressure with heat for meibomian gland drainage. The rolling action of the roller cylinder combined with the roller head to increase effectiveness in etnpting inspissated meibomian glands. The roller allows the patient to safely start the application of the pressure at the bottom of the glands and effectively roll open clogged oil glands. The washable roller keeps the head clean for long term use. A preheated eye-shaped soft gel pad can prepare the lids before the roller tip is applied by heating and softening the meibomian gland contents, allowing the roller to have a more effective action to induce mechanical extraction of the gland content.

18 Claims, 3 Drawing Sheets

(52) U.S. Cl.
CPC ............. *A61F 2007/0004* (2013.01); *A61F 2007/0078* (2013.01); *A61F 2007/0087* (2013.01); *A61F 2007/0095* (2013.01); *A61H 2015/0014* (2013.01); *A61H 2201/0207* (2013.01); *A61H 2201/0221* (2013.01); *A61H 2201/0228* (2013.01); *A61H 2201/0257* (2013.01); *A61H 2201/10* (2013.01); *A61H 2201/5082* (2013.01); *A61H 2205/024* (2013.01)

(58) Field of Classification Search
CPC ...... A61F 2007/0087; A61F 2007/0095; A61F 2007/0219; A61F 2007/0241; A61F 9/00718
See application file for complete search history.

(56) References Cited

U.S. PATENT DOCUMENTS

| | | | | |
|---|---|---|---|---|
| 5,979,006 | A * | 11/1999 | Stokes | A61H 11/00 15/222 |
| 6,648,904 | B2 * | 11/2003 | Altshuler | A46B 15/0036 492/46 |
| 9,216,028 | B2 * | 12/2015 | Korb | A61F 7/02 |
| 9,314,369 | B2 * | 4/2016 | Grenon | A61F 9/00772 |
| 9,719,977 | B2 * | 8/2017 | Korb | G01N 33/227 |
| 2013/0048011 | A1 * | 2/2013 | Bickford | A45D 34/041 132/320 |
| 2013/0172829 | A1 * | 7/2013 | Badawi | A61F 9/0008 604/294 |
| 2013/0197405 | A1 * | 8/2013 | Williams, III | A61H 15/0092 601/19 |
| 2013/0288859 | A1 * | 10/2013 | Watterson | A63B 24/0062 482/8 |
| 2014/0277303 | A1 * | 9/2014 | Biser | A61F 7/02 607/104 |
| 2015/0157112 | A1 * | 6/2015 | Daibes | A45D 44/06 132/229 |
| 2015/0165231 | A1 * | 6/2015 | Scheja | A61F 7/02 604/20 |
| 2015/0165238 | A1 * | 6/2015 | Slayton | A61B 18/18 601/2 |
| 2015/0182415 | A1 * | 7/2015 | Olkowski | A61H 23/02 601/93 |
| 2015/0320590 | A1 * | 11/2015 | Whitehurst | A61F 7/007 607/109 |
| 2016/0184162 | A1 * | 6/2016 | Grez | A61F 7/00 601/18 |

OTHER PUBLICATIONS

Qiao et al., "Emerging treatment options for meibomian gland dysfunction," Clinical Ophthalmology 2013(7): 1797-1803, Sep. 7, 2013.

* cited by examiner

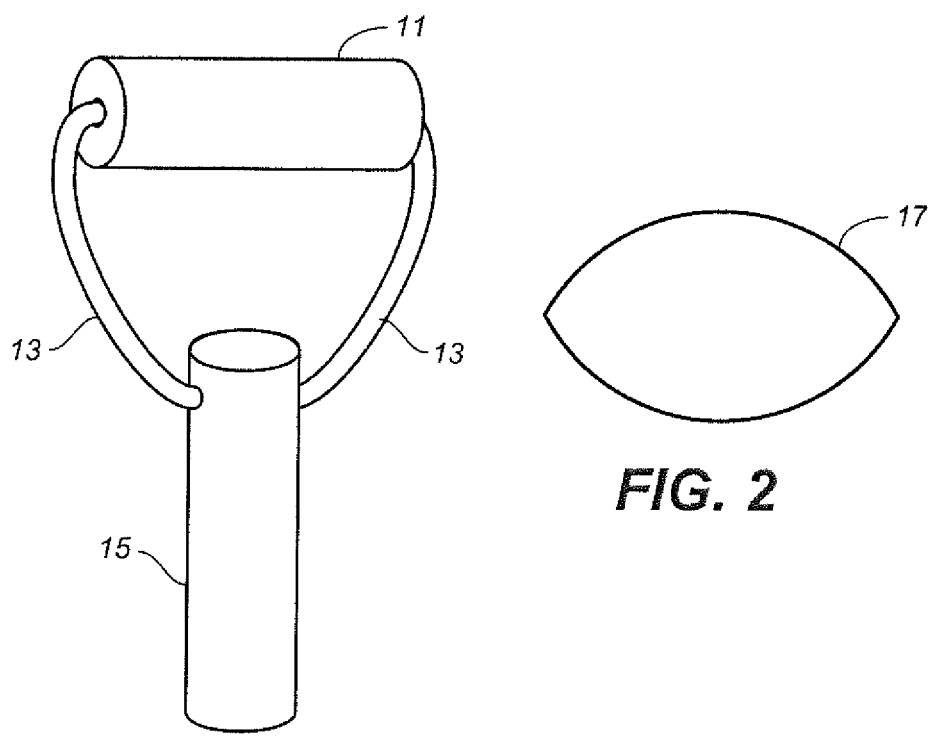
FIG. 1
FIG. 2
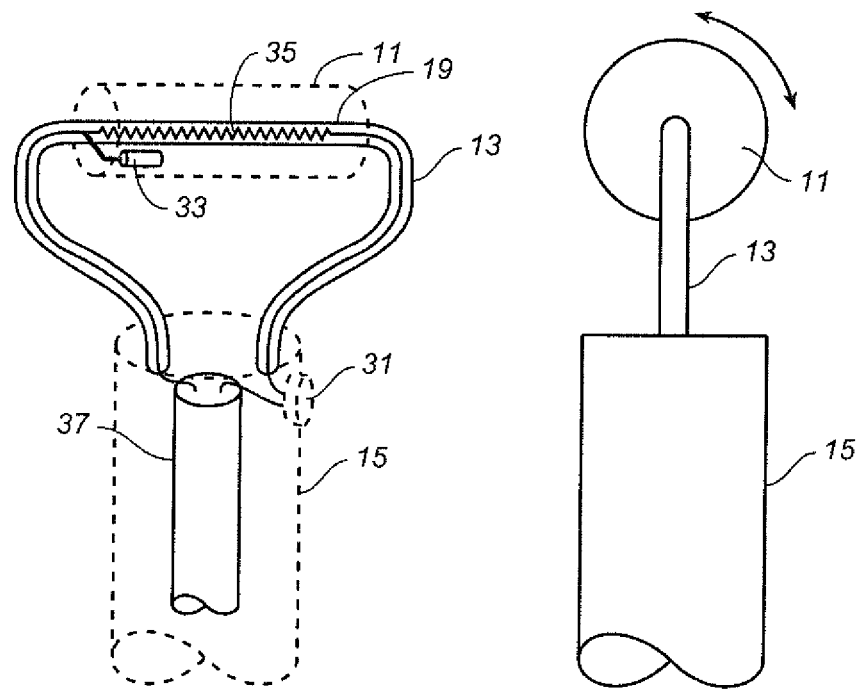
FIG. 3
FIG. 4

MEIBOMIAN GLAND ROLLER

CROSS-REFERENCE TO RELATED APPLICATIONS

This application claims priority from, U.S. Provisional Application No. 62/155,174, filed on Apr. 30, 2015, entitled "MG ROLLER," which is hereby incorporated in its entirety by this reference.

BACKGROUND

The following relates generally to the treatment of dry eyes and, more specifically, to the application of mechanical pressure for meibomian gland drainage.

The meibomian glands (or tarsal glands) are a type of sebaceous gland inside the substance of the eyelids responsible for the supply of meibum, an oily substance that prevents evaporation of the eye's tear film, Meibum prevents tear spillage onto the cheek, trapping tears between the oiled edge and the eyeball, and makes the closed lids airtight. Dysfunctional meibomian glands often cause city eyes, one of the more common eye conditions, Inflammation of the meibomian glands causes the glands to be obstructed by thick waxy secretions. Besides leading to dry eyes, the obstructions can result in other medical problems. Treatment can include expression of the gland by a professional. In some cases, antibiotics or steroids are prescribed.

SUMMARY

A roller includes a cylinder, an axel about which the cylinder can rotate, a handle, and arms. The cylinder and axel include a heating element, and the cylinder is configured to roll over and apply pressure to the eyelid of a user. The handle includes a power source and the axel is held to the handle by the arms and power is supplied by the arms from the power source to the heating element.

A method includes warming the cylinder of a roller, where the roller has a handle and arms by which the cylinder is attached to the handle. A user applies pressure to an eyelid of the user by the warmed cylinder and rolls the warmed roller across the user's eyelid to express the meibomian glands.

Various aspects, advantages, features and embodiments are included in the following description of exemplary examples thereof, which description should be taken in conjunction with the accompanying drawings. All patents, patent applications, articles, other publications, documents and things referenced herein are hereby incorporated herein by this reference in their entirety for all purposes. To the extent of any inconsistency or conflict in the definition or use of terms between any of the incorporated publications, documents or things and the present application, those of the present application shall prevail.

BRIEF DESCRIPTION OF THE DRAWINGS

FIG. 1 illustrates an embodiment of a meibomian gland roller.

FIG. 2 shows an example of an eye pad gel.

FIG. 3 includes some of the internal detail for the roller structure.

FIG. 4 is a side view of an embodiment of a meibomian gland roller.

DETAILED DESCRIPTION

Figure 5:
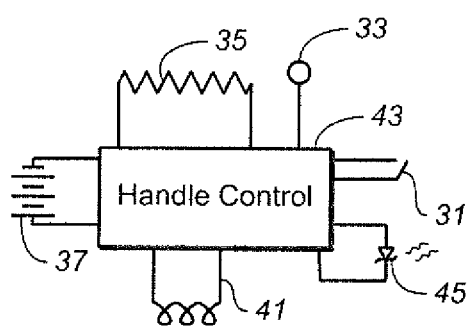
FIG. 5 is a schematic diagram of some electrical elements for an exemplary embodiment of the roller.

The Meibomian Gland Roller described here is a practical way to self-administer the treatment for one of the leading causes of dry eyes, namely, tear film oil deficiency. This roller combines an effective and safe method to use mechanical rolling pressure combined with heat for meibomian gland drainage. The roller can be distributed as a kit that is a complete package to melt, effectively and safely milk, and wash away the common hardened contents of a dysfunctional meibomian gland.

The device is designed with an externally-applied roller that can be applied to a closed eye that can be safely used by the consumer on their own eyelids without the need for a clinician inserting anything into the eye. Additionally, this roller can have an embedded sensor in the roller to control and maintain the temperature at the range of 42 to 45 degrees Celsius. Since eye shape and size vary from person to person, the roller head width will be designed to be about ⅓ of the width of the average adult person's eyelid size, on the order of 1-2 cm, for example. With this size roller, the device can be used on the eyelid of different size adult eyes, as well as the pediatric population.

The rolling action of this instrument, combined with the rolling head increases its effectiveness in empting inspissated meibomian glands. The roller tip allows the patient to safely start the application of the pressure at the bottom of the glands and effectively roll open the clogged up oil glands, analogous to squeezing out the contents of a tooth paste tube. The washable roller keeps the head clean for long term use. The removable roller head allows for a multi-user application.

A preheated, eye-shaped, soft gel pad can be used to prepare the lids by softening the meibomian gland contents and making it easier for the roller to have a more effective action to induce mechanical extraction of the gland content. As discussed below, a charging well structure can include a well for heating the eye-shaped gel pad. This allows for pads to be heated without use of a microwave to heat the gel pad, which makes it safer as well as more convenient to use. It is safer because no microwaves are used to heat up the gel before its application so close to the eye. It is more convenient since it can be used at any location simply by plugging it into an electric outlet or using the rechargeable battery. The gel pad can be designed to maintain the temperature between 42 and 45 degrees Celsius for 3 to 5 minutes or longer.

In one set of exemplary embodiments, the components of a roller system can include a heatable roller, having a roller cylinder and handle, a soft gel eye-pad, a charging base with a well for charging the roller, and a heating well for the soft gel eye pad.

FIG. 1 is a schematic element of the roller and eye pad. The roller includes a handle 15, arms 13, and a roller cylinder 11 supported on an axel (not visible in FIG. 1) held by the arms. The arms 13 hold the axel for the roller cylinder and attach to the handle 15, providing electric connections between the handle 15 and the axel and cylinder. The roller cylinder is the part that touches the eyelid. In a first exemplary embodiment, the roller cylinder is of a metal substance and attached to a chargeable handle to keep the roller at the temperature that corresponds to the melting point of the meibum and that is a safe temperature for the skin, such as 42 to 45 degrees Celsius, during application period. Electric power supplied can be supplied to a heating element in the roller by a battery in the handle to maintain this temperature range. The roller materials are preferably washable and comfortable against the skin. The roller can be packaged with additional rollers for future replacement. Also, replacement roller heads can optionally be bought or supplied. The soft gel eye pad 17 is shown in FIG. 2.

The roller cylinder can include the heating element and a temperature sensor to detect the temperature of the roller. Depending on the embodiment, the heating element can be part of the axle, part of the roller cylinder, or part of the surface of the roller cylinder or just below the surface of the roller cylinder. The temperature sensor, which, depending on the embodiment, is optional, can be located just below the surface of the roller cylinder or part of the axle, for example. The roller cylinder width will be designed to be about ⅓ of the width of the average adult person's eyelid size, on the order of 1-2 cm, for example.

The roller cylinder 11 can be made from metal with an appropriate thermal conductivity, silicone cast resin, or other materials, including Teflon,
Acrylic,
Bitumen,
Cellulose acetate, molded, sheet,
Granite,
Leather (dry),
Limestone,
Polycarbonate,
Polymethylmethacrylate,
Porcelain,
Polyvinylchloride (PVC),
Quartz mineral,
Silicone cast Resin, or
Vinyl ester.

A chargeable handle 15 for the roller can include a rechargeable battery, indicator light, and a switch that is controlled through a control button, as well as a connector to a well for charging the rechargeable battery. Alternately, wireless charging can be used. FIG. 3 corresponds to FIG. 1, but with some of the detail internal to both the roller 11 and handle 15 shown inside. The battery is shown at 37, where the wiring then runs through the arms 13 to the axel 19. Here the heating coil 35 is shown to be within the axel 19 and a temperature sensor circuit 33 is in the roller, A control button is represented on the handle at 31.

When the control button 31 is pressed, the switch can connect the rechargeable battery 37 to the heating element 35 and the temperature sensor 33 in the roller cylinder, and to the indicator light in the handle, to supply power to these three devices. When the roller is heated to the desired temperature, this is sensed by the temperature sensor, which can send a signal to the indicator light in the handle and to the charging base to so indicate. When the control button 31 is pressed again, the switch toggles and turns off the connection between the rechargeable battery and the heating element, the temperature sensor in the roller, and the indicator light in the handle. FIG. 4 is a side view corresponding to FIG. 1.

FIG. 5 is a schematic diagram of some electrical elements for an exemplary embodiment of the roller. The heating coil 35 and temperature sensor 33 are connected through the wiring in the arms to the handle's control circuitry 43. Depending on the embodiment, the rechargeable battery 37 can be charged through a connector or by way of an induction coil 41 for wireless charging. A LED 45 is included for an indicator light on the handle.

Figure 6:
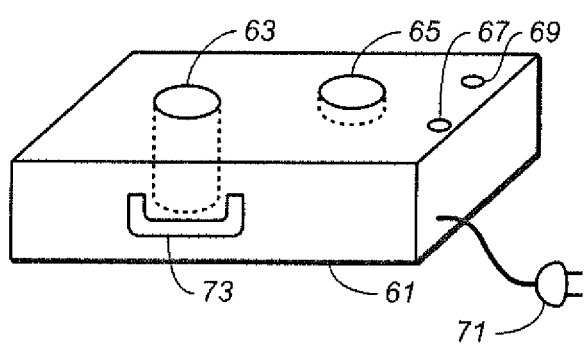
FIG. 6 shows an example of a charging well for the roller system.

FIG. 6 is a view for one embodiment of a charging base 61 with a roller well 63 and a heating well 65 for heating the soft gel eye pad, where an additional well can be included for an extra gel pad. The charging well 63 can include a socket for charging the handle, or an induction coil 73 for wireless charging. A cord 71 for connection to a power source. The charging base can also include a built in rechargeable. In this way, it can be used by simply plugging the cord 71 into an electric outlet, as well as using its rechargeable battery to operate it where there is no electricity available. The charging well can be equipped with an on-off switch (not shown) and an indicator light to signal when the arm and the pad are at the right temperature to be used.

The gel pad well 65 can heat the gel pad to the appropriate temperature. This allows the pad to be heated without use of a microwave oven, for example, as some people prefer not to heat using a microwave oven or it is not nearby to where the device is used. The flexible soft gel eye-shaped pad enclosing the gel can then be heated to 42-45 degrees Celsius before it is applied to the lids. A pair of indicator lights 67 and 69 can indicate the charge state or temperature for the handle and the temperature for gel eye pad.

Figure 7:
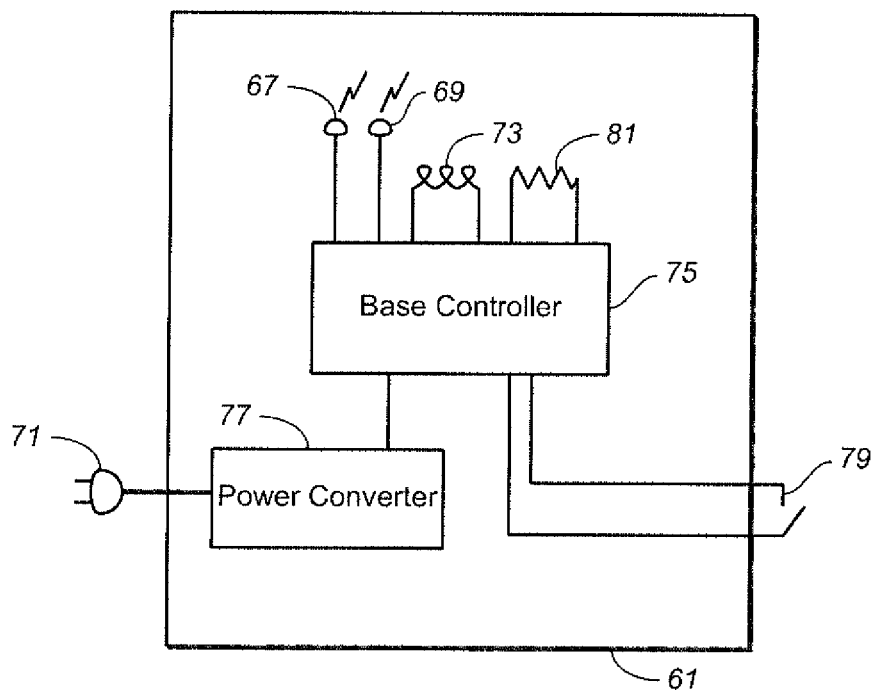
FIG. 7 is a schematic for some elements that can be in the base.

FIG. 7 is a schematic for some elements that can be in the base 61, A base controller 75 can be connected the lights 67 and 69 and induction coil 73, as well as a heating coil 81 for the gel pad. The cord 71 is connected to the power converter 77 that supplies power to the base, and an on-off switch is represented at 79.

The roller can also be used with sweeping applicators, which can be included in a kit with the roller and base, or obtained separately. The sweeping applicators can be individually foil-wrapped double ended sweepers with a presoaked gauze tips. The tips can be presoaked with a mild detergent and anti-bacterial solution.

In a typical application of the roller system, the charging base would be plugged in (or already plugged in), turned on, and the gel eye pad heated up to the right temperature. The indictor light can turn from red to green on the charging base, indicating that the desired temperature has been reached in the gel pad. The gel pad can then be applied on a closed eye for, say, two to three minutes, then removed from the eye, and placed back in the well to reheat it for the second eye. The roller can then be removed from the charging well, the indicator light on the handle having turned from red to green to indicate that the roller cylinder is in the proper temperature range. The user can then hold the handle firmly by hand, while in front of a mirror, and place the roller cylinder at the base of the lower lid and gently press on the lid and roll up towards the lashes. This motion can be repeated two to three times at each section of the lower lid until the user has covered the whole lid. The roller can then be applied to the upper lid, repeating the same steps as on the lower lid, except with a downward motion from the top of the upper eye lid towards the lashes. (The lower and upper eyelids can be done in either order.) The process is then repeated for the second eye. The user can then wash away the extruded meibomian gland debris with the presoaked sweeping applicators and wash the face with lukewarm water.

Figure 8:
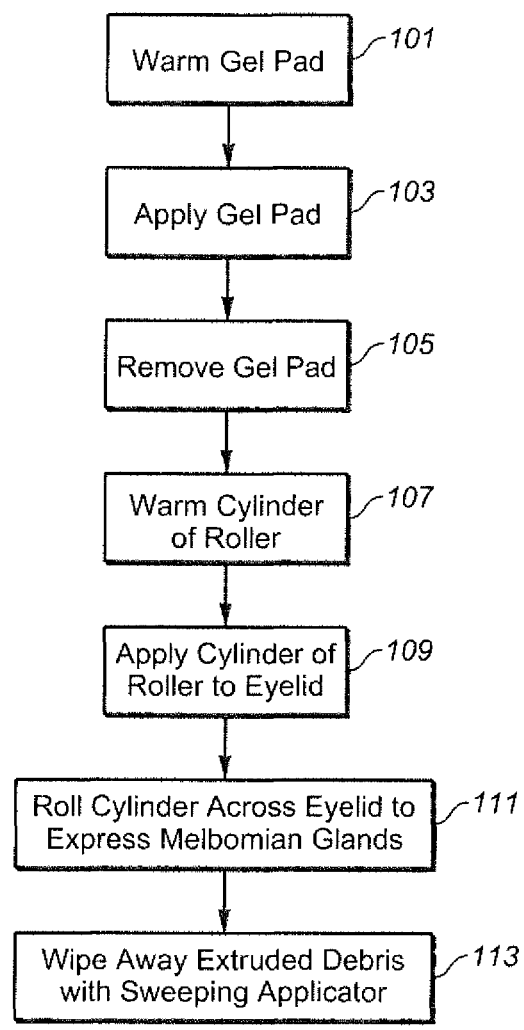
FIG. 8 is a flow to illustrate use of the meibomian gland roller.

FIG. 8 is a flow to illustrate use of the meibomian gland roller. At 101, the soft gel eye pad is heated, applied to the user's eye lid at 103, and then removed at 105. At 109, the cylinder of the roller is used to apply pressure to the user's eye lid, having previously been heated at 107. The user can then roll the cylinder across the user's eyelid at 111 to express the meibomian glands of the lid. At 113, the extruded meibomian gland debris is washed away with the sweeping applicators.

In an alternate set of embodiments, the heated roller can interface with a smartphone or similar device for power, communication, or both. For example, a smartphone application might be used to control and/or monitor its use and the frequency of use. Additionally, in some embodiments the handle could be connected to the smartphone to receive power.

The apparatus and techniques described above allow for the long term, regular maintenance of meibomian gland function by users themselves. Under previous arrangements, maintenance would involve going to a professional eye care practice for a patient to go through expensive meibomian gland drainage procedures. In between these procedures, which can be expensive, patients would rely upon maintenance procedures that can lack ease of use and that are of uncertain effectivity. In contrast, the procedures presented here are designed for ease of usage and effectiveness, allowing for a regular maintenance of the glands for an effective treatment regime.

The foregoing detailed description has been presented for purposes of illustration and description. It is not intended to be exhaustive or to limit the invention to the precise form disclosed. Many modifications and variations are possible in light of the above teaching. The described embodiments were chosen in order to best explain the principles involved and their practical application, to thereby enable others skilled in the art to best utilize the various embodiments and with various modifications as are suited to the particular use contemplated. It is intended that the scope of the invention be defined by the claims appended hereto.

It is claimed:

1. An eye treatment system comprising:
   an eye-shaped soft gel eye pad that is configured to be warmed and applied to an eyelid of a user;
   a handle including a power source;
   a charging well structure having:
   (a) a heating well configured to receive and heat the eye-shaped soft gel eye pad;
   (b) a charging well that receives a first end of the handle; and
   (c) an indicating light;
   a roller, comprising:
   an axle that includes a heating element, and
   a gel-filled cylinder that is configured to rotate about the axle, the gel-filled cylinder includes a temperature sensor that is adjacent a surface of the gel-filled cylinder for monitoring a temperature of the surface, and the temperature sensor is spaced apart from the heating element, and
   wherein the indicating light indicates when both the gel-filled cylinder is within a first temperature range and the eye-shaped soft gel eye pad is within a second temperature range, the gel-filled cylinder configured to roll over and apply pressure to the eyelid of the user; and
   arms by which the axle is held to a second end of the handle, opposite of the first end on the length of the handle, and by which power is supplied from the power source to the heating element, wherein wiring connecting the temperature sensor to control circuitry that is housed in the handle is routed via at least one of the arms.

2. The system of claim 1, wherein a temperature of the surface of the gel-filled cylinder from the heating element is regulated by the control circuitry and the temperature sensor.

3. The system of claim 1, wherein the heating element is housed in the axle.

4. The system of claim 3, wherein the heating element includes a heating coil.

5. The system of claim 1, wherein the gel-filled cylinder is formed from a metal substance.

6. The system of claim 1, wherein the gel-filled cylinder is replaceable.

7. The system of claim 1, wherein the power source is a rechargeable battery.

8. The system of claim 7, wherein the handle includes a connector whereby the rechargeable battery is rechargeable.

9. The system of claim 7, wherein the handle includes an inductance whereby the rechargeable battery is wirelessly rechargeable when the handle is placed in the charging well.

10. The system of claim 9, wherein the handle includes a second indicator light for indicating that the roller is within the first temperature range.

11. The system of claim 1, wherein the width of the gel-filled cylinder is in the 1-2 cm range.

12. The system of claim 1, wherein the handle is connectable to a smartphone to receive power and/or be controlled by an application on the smartphone.

13. A method, comprising:
   warming an eye-shaped soft gel eye pad in a heating well of a charging well structure;
   warming a gel-filled cylinder of a roller, the roller comprising the gel-filled cylinder, an axle, and a handle, the gel-filled cylinder connected to a first end of the handle by arms that hold the gel-filled cylinder, wherein a second end of the handle is configured to be placed in a roller well of the charging well structure;
   indicating, via an indicating light on the charging well structure, that the gel-filled cylinder is within a first temperature range and the eye-shaped soft gel eye pad is within a second temperature range;
   applying the warmed eye-shaped soft gel eye pad to an eyelid of a user;
   applying pressure, by the user, to the eyelid of the user by the warmed gel-filled cylinder;
   rolling by the user of the warmed roller across the eyelid of the user to express a meibomian gland thereof; and
   regulating a temperature of a surface of the gel-filled cylinder by a heating element that is included in the axle and a temperature sensor that is adjacent the surface of the gel-filled cylinder and the temperature sensor is spaced apart from the heating element, wherein wiring connecting the temperature sensor to control circuitry that is housed in the handle is routed via at least one of the arms.

14. The method of claim 13, further comprising:
   prior to applying the pressure, by the user, to the eyelid of the user by the warmed gel-filled cylinder, removing the eye-shaped soft gel eye pad from the eyelid of the user.

15. The method of claim 13, further comprising:
   subsequently washing away expressed meibomian gland debris.

16. The method of claim 13, wherein the gel-filled cylinder of the roller is warmed using a rechargeable battery charged by placing the second end of the handle in the roller well of the charging well structure.

17. The method of claim 13, wherein warming the gel-filled cylinder of the roller is performed in response to a smartphone application.

18. An eye treatment system comprising:
an eye-shaped soft gel eye pad that is configured to be warmed and applied to an eyelid of a user;
a handle housing a rechargeable battery and having a first end and a second end opposite the first end along the length of the handle, the first end configured to supply power to the rechargeable battery, the second end connected to arms holding an axle about which a gel-filled cylinder is configured to rotate,
the axle including a heating element, powered by the rechargeable battery, for heating the gel-filled cylinder, and
the gel-filled cylinder including a temperature sensor that is adjacent a surface of the gel-filled cylinder for monitoring a temperature of the surface of the gel-filled cylinder and that is spaced apart from the heating element, the gel-filled cylinder configured to roll over and apply pressure to the eyelid of the user when in use, wherein wiring connecting the temperature sensor to control circuitry that is housed in the handle is routed via at least one of the arms; and
a charging well structure having:
(a) a heating well configured to receive and heat the eye-shaped soft gel eye pad;
(b) a charging well configured to receive the first end of the handle and supply power to the rechargeable battery when the first end is placed in the charging well; and
(c) an indicating light for indicating when both the eye-shaped soft gel eye pad is within a first temperature range and when the temperature sensor indicates the gel-filled cylinder is within a second temperature range.

* * * * *